US005626864A

United States Patent [19]
Rosenberg et al.

[11] Patent Number: 5,626,864
[45] Date of Patent: May 6, 1997

[54] THE PREPARATION OF COLLOIDAL AQUEOUS SOLUTIONS OF ACTIVE SUBSTANCES OF LOW SOLUBILITY

[75] Inventors: Joerg Rosenberg, Ellerstadt, Germany; Cynthia Romerdahl, Wayland, Mass.; Juergen Heberger, Schifferstadt, Germany

[73] Assignee: Knoll Aktiengesellscahft, Ludwigshafen, Germany

[21] Appl. No.: 495,597

[22] PCT Filed: Feb. 7, 1994

[86] PCT No.: PCT/EP94/00332

§ 371 Date: Aug. 2, 1995

§ 102(e) Date: Aug. 2, 1995

[87] PCT Pub. No.: WO94/19018

PCT Pub. Date: Sep. 1, 1994

[30] Foreign Application Priority Data

Feb. 18, 1993 [DE] Germany ............ 43 05 003.5

[51] Int. Cl.$^6$ ............... A61K 47/24; A61K 47/26
[52] U.S. Cl. ............... 424/426; 514/937
[58] Field of Search ............ 424/426; 514/937; 252/302, 304, 306, 310, 314

[56] References Cited

U.S. PATENT DOCUMENTS

| | | | |
|---|---|---|---|
| 4,309,421 | 1/1982 | Ghyczy et al. | 514/78 |
| 4,482,474 | 11/1984 | Biedermann et al. | 252/311 |
| 5,008,050 | 4/1991 | Cullis et al. | 264/4.3 |
| 5,085,864 | 2/1992 | Cannon et al. | 424/450 |
| 5,432,196 | 7/1995 | Rosenberg et al. | 514/523 |

FOREIGN PATENT DOCUMENTS

| | | |
|---|---|---|
| 317120 | 5/1989 | European Pat. Off. . |
| 426029 | 5/1991 | European Pat. Off. . |
| 456106 | 11/1991 | European Pat. Off. . |
| 3010041 | 3/1980 | Germany . |
| 50-126821 | 10/1975 | Japan . |
| 93/01811 | 2/1993 | WIPO . |

OTHER PUBLICATIONS

Layton et al., *Europ. J. Cancer*, vol. 16, pp. 945–950.
J. Szejtli, *Pharm. Tech. Int.*, Feb. 1991, pp. 15–22.

*Primary Examiner*—John C. Bleutge
*Assistant Examiner*—Robert H. Harrison
*Attorney, Agent, or Firm*—Keil & Weinkauf

[57] ABSTRACT

A process with whose aid active substances of low solubility can be processed together with phospholipids to give a homogeneous solution, which comprises a) mixing the active substance with a phospholipid, b) adding an acidic aqueous solution of a carbohydrate to the residue at elevated temperature, and stirring this mixture at elevated temperature until a homogeneous colloidal solution is produced, and c) cooling the solution, and adjusting to a pH of 4–5 and sterilizing is described.

4 Claims, No Drawings

THE PREPARATION OF COLLOIDAL AQUEOUS SOLUTIONS OF ACTIVE SUBSTANCES OF LOW SOLUBILITY

The administration of a medicinal substance by, for example, injection or infusion into the bloodstream is often prevented by its low solubility in aqueous systems. This is why in recent years there has been development of various processes in order to formulate the medicinal substance in an aqueous phase with the aid of suitable solubilizers.

Most of the processes use for this purpose the solution-promoting effect of detergents or emulsifiers (cf. Voigt: Lehrbuch der pharmazeutischen Technologie, 5th edition, Verlag Chemie page 334). Although the preparation of such solutions is very straightforward, and a large number of medicinal substances can be solubilized in this way, the toxicity deriving from the detergents often entails considerable problems.

Another possibility is to mix the medicinal substances with cyclic carbohydrates (cyclodextrins) which complex the medicinal substance (Pharm. Techn. Intern., February 1991, page 15) and thus often crucially improve the solubility. However, since the internal cavity of cyclodextrins is limited, many molecules cannot be complexed for steric reasons, although the cyclodextrins are to be regarded as more toxicologically favorable than the detergents.

Another suitable class of solubilizers comprises the phospholipids which, as endogenous molecules (they are a constituent of every cell membrane), are very well tolerated even in injection solutions. The excellent tolerability of phospholipids has therefore led to them also being used in formulations of active substances which, although readily soluble in water, entail problems because of unacceptable local intolerance, eg. in the veins on intravenous administration. Improving the local tolerability by the choice of phospholipid formulations is known (Europ. J. Cancer; 16 (1980) 945–950). However, the use of phospholipids is often prevented by the fact that, in aqueous systems, they form not molecular solutions but only colloidal aggregates. However, these colloidal particles are so large when phospholipids are simply dispersed in aqueous solutions that such phospholipid-containing solutions cannot in general be used for preparations for injection and infusion (danger of embolism). The turbid solutions containing large colloidal particles which can be obtained by suspending phospholipids in aqueous systems must therefore be homogenized by suitable processes before they are used, so that the size of the particles in the solutions is reduced to values which permit the phospholipids to be used in injection or infusion solutions (U.S. Pat. No. 5,008,050).

Another disadvantage of phospholipid-containing solutions is that sterilization of the finished solutions in the final container by autoclaving almost always results in the phospholipids flocculating out.

Various processes are known for bringing the large size of the colloidal particles in phospholipid solutions into the submicrometer range. These include established laboratory methods such as sonication, but also processes on the production scale such as high-pressure homogenization. However, these methods are relatively expensive.

The present invention relates to a process with whose aid active substances of low solubility can be processed together with phospholipids to give a homogeneous solution, which comprises a) mixing the active substance with a phospholipid, b) adding a strongly acidic aqueous solution of a carbohydrate to the residue at elevated temperature, and stirring this mixture at elevated temperature until a homogeneous colloidal solution is produced, and c) cooling the solution, and adjusting to a pH of 4–5 and sterilizing.

The novel process is suitable for basic active substances which have nitrogen atoms which can be protonated in acids and which are in ionic form in the acidic pH range, such as active substances containing basic amino groups which can be protonated. These compounds are often relatively readily soluble in water at strongly acidic pH values but crystallize out again, substantially in the form of the bases, on titration to weakly acidic to neutral pH values.

The process is particularly suitable for cationic active substances (which can be protonated) which have a solubility of less than 1 mg/ml in water even in the form of their salts (with inorganic or organic counter ions).

Examples of active substances of this type are the bisnaphthalimides of U.S. Pat. No. 4,874,683. These bisnaphthalimides often have low solubility in water (<1 mg/ml) even in the form of their salts (eg. methanesulfonates). On the other hand, when the pH is lowered the solubility increases greatly, as expected. However, solutions with these low pH values cannot be administered.

Other examples are highly lipophilic active substances of the anipamil hydrochloride type, and the active substances of EP 363 212; both classes of active substance have low solubility in water.

Nonionic active substances, by contrast, cannot be converted using the process according to the invention because, in this case, the ionization, in initially strongly acidic medium, which is necessary for the solubilization is impossible because of the absence of a functional group which can be protonated. Similar is true of anionic active substances because, although they can be protonated in strongly acidic medium, they are then in nonionic form, which reduces the solubility in water.

Besides the cationic active substances which have low solubility (at neutral pH), however, the process can also be applied to those substances which, although adequately soluble in water, show problems due to local intolerance on administration (eg. vein irritation on intravenous administration). Examples of active substances of this type are levemopamil hydrochloride, dexverapamil hydrochloride and water-soluble bisnaphthalimides which, because of the absence of the aromatic nitro substituents, are readily soluble in water.

All natural (ie. isolated from natural raw materials) or synthetically prepared phospholipids are suitable for the process according to the invention. Mixtures of various phospholipids are also possible. Particularly preferred phospholipid mixtures are those isolated from soybean or egg yolk ("soybean lecithin", "egg lecithin"), especially when these contain more than about 80% phosphatidylcholine.

The phospholipid:active substance ratio can be from 20:1 to 1:1, preferably 10:1 to 5:1, by weight. The ratio most suitable for the particular active substance must be established empirically. The phospholipid content of the finished solution is from 10 to 150 mg/ml, preferably from 20 to 60 mg/ml.

Intimate mixing of active substance and phospholipid can most simply be carried out by dissolving them together in an organic solvent and subsequently removing the solvent. In many cases it is sufficient simply to mix the active substance and phospholipid without a previous dissolving step.

Carbohydrates which can be used are all pharmaceutically customary mono- and disaccharides. Examples thereof are the substances listed in the relevant pharmacopeias, eg. glucose, fructose etc. However, sugar alcohols and other polyhydroxy compounds are also suitable. Examples thereof are sorbitol, xylitol, mannitol and glycerol. Among the carbohydrates, the disaccharides are preferred, especially sucrose, trehalose and maltose. Among the polyhydroxy compounds, glycerol and mannitol are preferred. The carbohydrates are added to the formulations in amounts such that the finished solutions are substantially isotonic with blood, ie. they are simultaneously used to isotonicize the solutions to an osmotic pressure approximately corresponding to that of blood.

The aqueous solutions of the carbohydrates ought to have a pH of from 1.5 to 2.5. The mixture dissolves best at from 30° to 60° C.

The pH is kept constant in the solution after titration is complete by adding suitable buffer substances. It has emerged that the stability of the preparations according to the invention is best at a pH of about 4 to 5. Lower pH values may lead to intolerance reactions on administration (especially on injection into the bloodstream), whereas at neutral pH the active substance flocculates out after 12–24 hours. Preferred buffer substances therefore have a maximum buffer capacity (pKa) in the pH range from 4 to 5. These include, in particular, the mono- and dicarboxylic acids used in drug formulation, such as acetic acid, succinic acid, but also hydroxy carboxylic acids such as citric acid, tartaric acid, malic acid and lactic acid, and amino acids such as glycine and aspartic acid. Acetic acid is particularly preferred. The buffer substances are added to the preparations according to the invention preferably in concentrations of about 10 mmol per liter.

To improve the storage stability, it is advisable to add heavy metal chelators such as ethylenediaminetetraacetic acid (EDTA, as Na salt) and antioxidants such as tocopherol (or tocopherol derivatives) to the solutions. The amounts used for this purpose correspond to those used for pharmaceutically customary injection solutions.

It was surprising that the use of the process according to the invention results in phospholipid-containing solutions in which the particle sizes of the phospholipid aggregates are so low that sterile filtration through 0.2 µm filters is generally possible immediately after preparation. Such particle sizes in phospholipid-containing solutions can otherwise be obtained only by more elaborate processes (sonication, high-pressure homogenization).

The final sterilization in the final container can be carried out by known processes such as autoclaving, without the phospholipids flocculating out.

Furthermore, the solutions remain stable over a long period without flocculation out occurring.

The following examples illustrate the invention. The criterion for successful solubilization is the possibility of sterile filtration through a 0.2 µm filter.

EXAMPLE 1

U.S. Pat. No. 4,874,683 describes active substances which have a bisnaphthalimide structure. Because of the very low solubility in water, it is very difficult to prepare sufficiently concentrated aqueous solutions of active substance. Although it is possible to prepare injection solutions with the assistance of solubilizers such as dimethyl sulfoxide, the active substance rapidly flocculates out of these again after injection in the blood.

A derivative of these bisnaphthalimides was used to investigate the solubility in aqueous formulations as follows:

Experiment A (Comparative Experiment)

40 mg of Z were dissolved in 10 ml of dichloromethane/methanol (9+1). All the solvent was removed again from the solution in a rotary evaporator under reduced pressure. 8 ml of a buffer solution (consisting of o-phsophoric acid [0.01 M] and sucrose [0.265 M] and EDTA disodium salt [0.1 mg/ml], pH about 1.9) were added to the residue, and the flask was rotated on the rotary evaporator (without reducing the pressure) with the water at 50° C for 1 h. It was possible in this way to dissolve a considerable portion of the active substance. Cooling to room temperature was followed by titration with 2 molar sodium hydroxide solution to pH 6.8, and the total volume was then made up to 10 ml with the abovementioned buffer solution (pH 6.8; titrated with NaOH). Most of the active substance precipitated again. The clear supernatant was filtered through a 0.2 micrometer syringe filter, and the active substance concentration in this solution was determined by spectrophotometry. The active substance content in this solution was below 0.1 mg/ml.

Experiment B (Comparative Experiment)

The experiment was carried out like experiment A but 1.0 g of phospholipid (egg lecithin E 100, from Lipoid KG, Ludwigshafen) was weighed in in addition to the active substance.

The active substance content of the solution which had been titrated to pH 6.8 and sterilized by filtration was 4.0 mg/ml. The solution slowly flocculated out after about 12–24 h, both at room temperature and in a refrigerator.

Experiment C

The experiment was carried out like experiment B, but after addition of the buffer solution (pH 1.9) and stirring at 50° C. (1 h), 100 microliters of a dilute aqueous solution of glacial acetic acid (120.1 g/l) were added, and this solution was then titrated to pH 4.6 with sodium hydroxide solution (2 molar).

The active substance content of this solution after sterile filtration was 4.0 mg/ml. The solutions were all stable for weeks without flocculating out, both at room temperature and in a refrigerator.

EXAMPLE 2

The example was carried out like Example 1, experiment C, but with 5.5 mg/ml of levemopamil hydrochloride and 30.0 mg of egg lecithin E 100. The pH was adjusted to 4.8.

The finished solution was sterilized by stepwise filtration (firstly 0.45 µm, then 0.2 µm).

Comparative Example

The nonionic active substance esuprone (EP 111.746, Example 30), whose solubility in water is only 15 µg/ml,

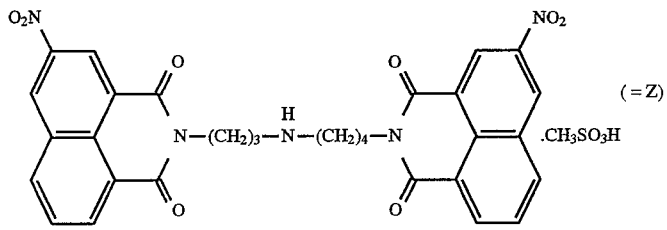

was subjected to an experiment like Example 1, experiment C. The resulting solution contained large colloidal particles and could not be filtered either through a 0.2 μm filter or through a 0.45 μm filter.

EXAMPLE 3

The hydrophobic peptide dolastatin 15 which has low solubility in water was subjected to an experiment like the comparative example. The active substance content was 10 mg/ml, and the phospholipid content was 100 mg/ml. It was possible to sterilize the solution by filtration.

EXAMPLE 4

Example 3 was repeated but the active substance used was the compound

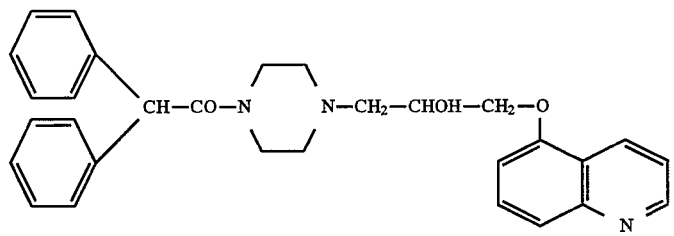

in the form of the monofumarate (EP 363 212). It was possible to sterilize the resulting solution by filtration.

EXAMPLE 5

Example 3 was repeated but dexverapamil hydrochloride (=R-verapamil×HCl) was used as active substance in an amount of 20 mg/ml. It was possible to sterilize the resulting solution by filtration.

We claim:
1. A process for the production of unaggregated homogeneous emulsions of basic active substances having nitrogen atoms protonatable in acids and in ionic form at acidic pH, with phospholipids which comprises
   a) creating a mixture comprising an active substance and a phospholipid by dissolving the active substance and the phospholipid in an organic solvent and then removing the solvent; or by mixing the active substance and the phospholipid without a solvent, and then
   b) adding an acidic aqueous solution of a carbohydrate to the mixture at an elevated temperature, and stirring this mixture at said temperature until a homogeneous colloidal emulsion is produced; and then
   c) cooling the emulsion, adjusting to pH 4–5;
   wherein said pH-adjusted emulsion is able to pass through a filter having a pore size of 0.2 μm.

2. A process as defined in claim 1, wherein in step a) the mixture of the active substance and the phospholipid is created without a solvent.

3. A process as defined in claim 1, wherein in step a) the mixture is created by dissolving the active substances and the phospholipid in an organic solvent and then removing the solvent.

4. A process as defined in claim 1 wherein the temperature in step b) is between 30° to 60° C.

* * * * *